(12) United States Patent
Ishii et al.

(10) Patent No.: US 7,608,727 B2
(45) Date of Patent: Oct. 27, 2009

(54) PROCESS FOR THE PREPARATION OF FURAN COMPOUNDS

(75) Inventors: Yasutaka Ishii, Takatsuki (JP); Tatsuya Nakano, Himeji (JP); Takahiro Iwahama, Himeji (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 0 days.

(21) Appl. No.: 11/709,203

(22) Filed: Feb. 22, 2007

(65) Prior Publication Data

US 2007/0197806 A1    Aug. 23, 2007

(30) Foreign Application Priority Data

Feb. 23, 2006  (JP)  ............................. 2006-046310
Dec. 25, 2006  (JP)  ............................. 2006-348652

(51) Int. Cl.
*C07D 307/40*  (2006.01)
*C07D 307/54*  (2006.01)

(52) U.S. Cl. ................... 549/486; 549/474; 549/483

(58) Field of Classification Search ............... 549/498, 549/505, 508, 456, 471, 486, 474, 483
See application file for complete search history.

(56) References Cited

FOREIGN PATENT DOCUMENTS

| EP | 0 031 729 A1 | 7/1981 |
| EP | 1 178 031 A1 | 2/2002 |
| EP | 1 342 711 A2 | 9/2003 |
| EP | 1 535 915 A1 | 6/2005 |
| WO | WO-98/52558 A1 | 11/1998 |

OTHER PUBLICATIONS

Konig B., Science of Synthesis, "Product Class 9: Furans", vol. 9, 2001, 183-285.*
Koenig B., "Product Class 9: Furans" Science of Synthesis, vol. 9, 2001, pp. 183-285.
Luo et al., J. Org. Chem., vol. 64, 1999, pp. 1738-1740.
Kotsuki et al., "Efficient Synthesis of Acetoxyfimbrolides and Beckerelides Analogs," Chemistry Letters, (1983), pp. 1007-1008.

* cited by examiner

*Primary Examiner*—Bernard Dentz
(74) *Attorney, Agent, or Firm*—Birch, Stewart, Kolasch & Birch, LLP

(57) ABSTRACT

A carbonyl compound represented by following Formula (1):

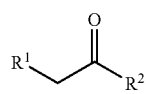

(1)

wherein $R^1$ represents hydrogen atom or an organic group; and $R^2$ represents hydrogen atom or an organic group having a carbon atom at a bonding site with the carbonyl group in Formula (1), wherein $R^1$ and $R^2$ may be combined to form a ring with adjacent two carbon atoms, or an equivalent thereof is reacted with an unsaturated compound represented by following Formula (2):

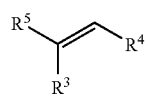

(2)

wherein each of $R^3$, $R^4$, and $R^5$ represents hydrogen atom, a halogen atom, hydroxyl group, or an organic group and wherein $R^3$ and $R^4$ may be combined to form a ring with adjacent two carbon atoms, or a precursor thereof, to yield a furan compound represented by following Formula (3):

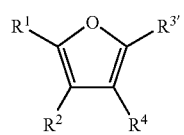

(3)

wherein $R^{3\prime}$ represents $R^3$, $R^5$ or hydrogen atom; and $R^1$, $R^2$, $R^3$, $R^4$, are $R^5$ are as defined above.

9 Claims, No Drawings

PROCESS FOR THE PREPARATION OF FURAN COMPOUNDS

BACKGROUND OF THE INVENTION

1. Field of the Invention

The present invention relates to processes for the preparation of furan compounds. More specifically, it relates to a process for the preparation of furan compounds, in which a carbonyl compound or an equivalent thereof is allowed to react with an unsaturated compound having a carbon-carbon double bond, or a precursor thereof. Such furan compounds are useful typically as raw materials for polymers, intermediates for the synthetic preparation of highly functional materials and fine chemicals such as dyestuffs, pharmaceutical preparations, and bioactive substances, and intermediate materials for other organic chemicals.

2. Description of the Related Art

Furan compounds have been prepared, for example, by a process in which a 1,4-dicarbonyl compound as a starting material is subjected to cyclization-dehydration in the presence of an acid catalyst (Chem., Lett., 1983, 1007). This process, however, uses a hardly-available raw material, is not a versatile technique, and is thereby not an industrially efficient process for producing furan compounds.

SUMMARY OF THE INVENTION

Under these circumstances, it is desirable to provide a process for industrially efficiently preparing furan compounds from easily available raw materials. It is also desirable to provide a versatile process for preparing furan compounds.

After intensive investigations, the present inventors have found that a cyclization reaction as a result of coupling smoothly proceeds to yield a corresponding furan compound in a good yield by allowing a carbonyl compound, such as an aldehyde, or an equivalent thereof to react with an unsaturated compound having a carbon-carbon double bond, such as an acrylic ester, or a precursor thereof. The present invention has been made based on these findings.

According to an embodiment of the present invention, there is provided a process for the preparation of a furan compound. The process includes the step of carrying out a reaction of a carbonyl compound represented by following Formula (1):

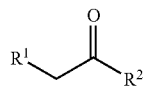

(1)

wherein $R^1$ represents hydrogen atom or an organic group; and $R^2$ represents hydrogen atom or an organic group having a carbon atom at a bonding site with the carbonyl group in Formula (1), wherein $R^1$ and $R^2$ may be combined to form a ring with adjacent two carbon atoms, or an equivalent thereof, with an unsaturated compound represented by following Formula (2):

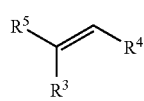

(2)

wherein each of $R^3$, $R^4$, and $R^5$ represents hydrogen atom, a halogen atom, hydroxyl group, or an organic group and wherein $R^3$ and $R^4$ may be combined to form a ring with adjacent two carbon atoms, or a precursor thereof, to yield a furan compound represented by following Formula (3):

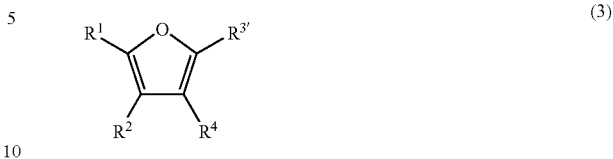

(3)

wherein $R^{3'}$ represents $R^3$, $R^5$ or hydrogen atom; and $R^1$, $R^2$, $R^3$, $R^4$, are $R^5$ are as defined above. The heteropolyacid or a salt thereof (B1) preferably contains an element selected from phosphorus and silicon and at least one element selected from vanadium, molybdenum, and tungsten as constitutional elements. The heteropolyacid or a salt thereof (B1) may be a phosphovanadomolybdic acid or phosphomolybdic acid represented by following Formula:

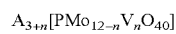

$A_{3+n}[PMo_{12-n}V_nO_{40}]$ wherein "A" represents at least one selected from hydrogen atom, $NH_4$, alkali metals, and alkaline earth metals; and "n" represents an integer of 0 to 10, or a salt of them.

The reaction is also preferably carried out in the presence of a Lewis acid (C) in addition to the catalytic palladium compound (A).

An unsaturated compound represented by Formula (2) is preferably a compound in which $R^4$ is an electron-withdrawing group.

A process according to an embodiment of the present invention can industrially efficiently produce furan compounds from easily available raw materials. Such a process is highly versatile and can easily and conveniently produce furan compounds having various substituents.

DESCRIPTION OF THE PREFERRED EMBODIMENTS

Reaction Components

According to an embodiment of the present invention, a carbonyl compound represented by Formula (1) or an equivalent thereof is allowed to react with an unsaturated compound represented by Formula (2) or a precursor thereof.

In Formula (1), $R^1$ represents hydrogen atom or an organic group; and $R^2$ represents hydrogen atom or an organic group having a carbon atom at a bonding site with the carbonyl group in Formula (1), and $R^1$ and $R^2$ may be combined to form a ring with adjacent two carbon atoms. Such organic groups can be any organic groups that do not adversely affect the reaction. Examples thereof include hydrocarbon groups, heterocyclic groups, substituted oxy groups, N-substituted amino groups, acyl groups and carbonyl-protected derivatives thereof, substituted oxycarbonyl groups, carboxyl group, substituted or unsubstituted carbamoyl groups, cyano group, substituted or unsubstituted iminoalkyl groups, sulfur acid ester groups, and groups containing two or more of these groups combined with each other. The carboxyl group and other groups may be protected by protecting groups. These organic groups may each have any number of carbon atoms, may have, for example, about one to about twenty carbon atoms, and preferably have about one to about ten carbon atoms.

The hydrocarbon groups include aliphatic hydrocarbon groups, alicyclic hydrocarbon groups, and aromatic hydrocarbon groups. The aliphatic hydrocarbon groups include, for example, straight- or branched-chain aliphatic hydrocarbon groups (alkyl groups, alkenyl groups, and alkynyl groups) having about one to about twenty carbon atoms, such as methyl, ethyl, propyl, isopropyl, butyl, isobutyl, s-butyl, t-butyl, pentyl, hexyl, octyl, decyl, tetradecyl, hexadecyl, octadecyl, vinyl, allyl, 1-propenyl, and ethynyl groups. Among them, those having about one to about ten carbon atoms are preferred, and those having about one to about six carbon atoms are more preferred.

The alicyclic hydrocarbon groups include, for example, alicyclic hydrocarbon groups such as cycloalkyl groups, cycloalkenyl groups, and bridged hydrocarbon groups, each having about three to about twenty carbon atoms. Examples thereof are cyclopropyl, cyclobutyl, cyclopentyl, cyclohexyl, cyclohexenyl, cyclooctyl, cyclodecyl, cyclododecyl, adamantyl, and norbornyl groups. Among them, those having about three to about fifteen carbon atoms are preferred.

The aromatic hydrocarbon groups include, for example, aromatic hydrocarbon groups having about six to about twenty carbon atoms, such as phenyl and naphthyl groups.

These hydrocarbon groups may each have one or more substituents. Examples thereof are halogen atoms (fluorine, chlorine, bromine, and iodine atoms), oxo group, protected or unprotected hydroxyl groups, protected or unprotected hydroxymethyl groups, protected or unprotected amino groups, protected or unprotected carboxyl groups, substituted oxycarbonyl groups, substituted or unsubstituted carbamoyl groups, nitro group, acyl groups, cyano group, and heterocyclic groups. The protecting groups herein can be conventional protecting groups used in organic synthesis.

Of these organic groups, heterocyclic groups contain heterocyclic rings such as aromatic heterocyclic rings and non-aromatic heterocyclic rings. Such heterocyclic rings include, for example, heterocyclic rings containing oxygen atom as a hetero atom, including five-membered rings such as furan, tetrahydrofuran, oxazole, and isoxazole, six-membered rings such as 4-oxo-4H-pyran, tetrahydropyran, and morpholine, fused rings such as benzofuran, isobenzofuran, 4-oxo-4H-chromene, chroman, and isochroman; heterocyclic rings containing sulfur atom as a hetero atom, including five-membered rings such as thiophene, thiazole, isothiazole, and thiadiazole, six-membered rings such as 4-oxo-4H-thiopyran, and fused rings such as benzothiophene; heterocyclic rings containing nitrogen atom as a hetero atom, including five-membered rings such as pyrrole, pyrrolidine, pyrazole, imidazole, and triazole, six-membered rings such as pyridine, pyridazine, pyrimidine, pyrazine, piperidine, piperazine, and fused rings such as indole, indoline, quinoline, acridine, naphthyridine, quinazoline, and purine. The heterocyclic groups may each have one or more substituents. Such substituents include the substituents which the hydrocarbon groups may have, as well as alkyl groups including alkyl groups having about one to about four carbon atoms, such as methyl and ethyl groups; cycloalkyl groups; and aryl groups such as phenyl and naphthyl groups.

Of the organic groups, the substituted oxy groups include, for example, alkoxy groups such as methoxy, ethoxy, propoxy, and butoxy groups, of which alkoxy groups having about one to about ten carbon atoms are preferred; aryloxy groups such as phenoxy, and naphthyloxy groups; aralkyloxy groups such as benzyloxy group; cycloalkyloxy groups such as cyclohexyloxy group; and acyloxy groups such as acetoxy, propionyloxy, butyryloxy, (meth)acryloyloxy, cyclohexanecarbonyloxy, and benzoyloxy groups, of which acyloxy groups having about one to about ten carbon atoms are preferred. The N-substituted amino groups include, for example, N,N-dimethylamino, N,N-diethylamino, and piperidino groups.

The acyl groups include, for example, aliphatic, alicyclic, aromatic or heterocyclic acyl groups such as formyl, acetyl, propionyl, butyryl, (meth)acryloyl, cyclopentanecarbonyl, cyclohexanecarbonyl, benzoyl, naphthoyl, and pyridylcarbonyl groups, of which acyl groups having about one to about ten carbon atoms are preferred. Carbonyl-protected derivatives of acyl groups include acetals such as dimethylacetal, diethylacetal, 1,3-dioxane, and 1,3-dioxolane; and dithioacetals such as S,S'-dimethyldithioacetal.

The substituted oxycarbonyl groups include, for example, alkoxycarbonyl groups such as methoxycarbonyl, ethoxycarbonyl, isopropoxycarbonyl, and butoxycarbonyl groups; alkenyloxycarbonyl groups such as vinyloxycarbonyl group; cycloalkyloxycarbonyl groups such as cyclopentyloxycarbonyl and cyclohexyloxycarbonyl groups; aryloxycarbonyl groups such as phenoxycarbonyl group; aralkyloxycarbonyl groups such as benzyloxycarbonyl group; heterocyclic ring-oxycarbonyl groups such as pyridyloxycarbonyl group; and acyloxycarbonyl groups (acid anhydride groups).

The substituted or unsubstituted carbamoyl groups include, for example, carbamoyl, N-methylcarbamoyl, N-phenylcarbamoyl, N,N-dimethylcarbamoyl, 1-pyrrolidinylcarbonyl, and piperidinocarbonyl groups. The sulfur acid ester groups include sulfonic ester groups such as methyl sulfonate and ethyl sulfonate groups; and sulfinic ester groups such as methyl sulfinate and ethyl sulfinate groups.

$R^1$ and $R^2$ may be combined to form a ring with adjacent two carbon atoms. Such rings include alicyclic carbon rings having about three to about twenty members, such as cycloalkane rings, cycloakene rings, and bridged carbon rings. Specific examples thereof include cyclopropane, cyclobutane, cyclopentane, cyclopentene, cyclohexane, cyclohexene, cyclooctane, cyclododecane, and norbornene rings. These rings may each have one or more substituents and/or may further have other rings (nonaromatic rings or aromatic rings) fused thereto.

Preferred examples of $R^1$ include hydrogen atom; substituted or unsubstituted hydrocarbon groups including aliphatic hydrocarbon groups having about one to about twenty carbon atoms, of which those having about one to about ten carbon atoms are preferred, aromatic hydrocarbon groups having about six to about twenty carbon atoms, such as phenyl group and naphthyl group, alicyclic hydrocarbon groups having about three to about twenty carbon atoms such as cycloalkyl groups having about three to about eight members, and bridged hydrocarbon groups, and haloalkyl groups including haloalkyl groups having about one to about six carbon atoms, such as trifluoromethyl group, of which haloalkyl groups having about one to about four carbon atoms are preferred; heterocyclic groups; substituted oxy groups including alkoxy groups having about one to about ten carbon atoms, aryloxy groups, aralkyloxy groups, cycloalkyloxy groups, and acyloxy groups having about one to about ten carbon atoms; acyl groups; carbonyl-protected acyl groups; substituted oxycarbonyl groups including alkoxy-carbonyl groups having about one to about six carbon atoms in the alkoxy moiety, aryloxycarbonyl groups, aralkyloxycarbonyl groups, and cycloalkyloxycarbonyl groups; carboxyl group; substituted or unsubstituted carbamoyl groups; cyano group; and sulfur acid ester groups.

Preferred examples of $R^2$ include hydrogen atom; substituted or unsubstituted hydrocarbon groups including aliphatic hydrocarbon groups having about one to about twenty carbon atoms, of which those having about one to about ten carbon atoms are preferred, aromatic hydrocarbon groups having about six to about twenty carbon atoms, such as phenyl group and naphthyl group, alicyclic hydrocarbon groups having about three to about twenty carbon atoms such as cycloalkyl groups having about three to about eight members, and bridged hydrocarbon groups, and haloalkyl groups including haloalkyl groups having about one to about six carbon atoms, such as trifluoromethyl group, of which haloalkyl groups having about one to about four carbon atoms are preferred; and heterocyclic groups.

Representative examples of carbonyl compounds represented by Formula (1) include aldehydes such as acetaldehyde, propionaldehyde, butyraldehyde, isobutyraldehyde, amylaldehyde, isoamylaldehyde, hexanal, heptanal, decanal, dodecanal, and phenylacetaldehyde; and ketones including chain ketones and cyclic ketones, such as acetone, ethyl methyl ketone, diethyl ketone, methyl propyl ketone, butyl methyl ketone, pentyl methyl ketone, hexyl methyl ketone, octyl methyl ketone, decyl methyl ketone, cyclopentanone, cyclohexanone, methylcyclohexanone, cycloheptanone, cyclooctanone, and cyclododecanone. Equivalents of carbonyl compounds represented by Formula (1) include compounds that yield the same reaction products as carbonyl compounds represented by Formula (1), including multimers such as paraldehyde (trimer of acetaldehyde); and carbonyl-protected derivatives.

In Formula (2), each of $R^3$, $R^4$, and $R^5$ represents hydrogen atom, a halogen atom, hydroxyl group, or an organic group, in which $R^3$ and $R^4$ may be combined to form a ring with adjacent two carbon atoms. The positions of $R^3$ and $R^5$ in Formula (2) may be reversed.

The halogen atom includes, for example, chlorine atom, bromine atom, and iodine atom. The organic group are as with those mentioned above. $R^3$ and $R^4$ may be combined to form a ring with adjacent two carbon atoms. The ring herein includes the rings listed as the ring formed by $R^1$ and $R^2$ with adjacent two carbon atoms.

Preferred examples of $R^3$, $R^4$, and $R^5$ include hydrogen atom; halogen atoms; substituted or unsubstituted hydrocarbon groups including aliphatic hydrocarbon groups having about one to about twenty carbon atoms, of which those having about one to about ten carbon atoms are preferred, aromatic hydrocarbon groups having about six to about twenty carbon atoms, such as phenyl group and naphthyl group, alicyclic hydrocarbon groups having about three to about twenty carbon atoms such as cycloalkyl groups having about three to about eight members, and bridged hydrocarbon groups, and haloalkyl groups including haloalkyl groups having about one to about six carbon atoms, such as trifluoromethyl group, of which haloalkyl groups having about one to about four carbon atoms are preferred; substituted or unsubstituted heterocyclic groups; substituted oxy groups including alkoxy groups having about one to ten carbon atoms, aryloxy groups, aralkyloxy groups, cycloalkyloxy groups, and acyloxy groups having about one to about ten carbon atoms; acyl groups; carbonyl-protected acyl groups; substituted oxycarbonyl groups including alkoxy-carbonyl groups having about one to about six carbon atoms in the alkoxy moiety, aryloxycarbonyl groups, aralkyloxycarbonyl groups, and cycloalkyloxycarbonyl groups; carboxyl group; substituted or unsubstituted carbamoyl groups; cyano group; and sulfur acid ester groups. Compounds of Formula (2) in which $R^3$ or $R^5$ is hydroxyl group are also preferred. In this case, the compounds represented by Formula (2) are enol compounds.

When $R^5$ is hydrogen atom, $R^3$ can be any of hydrogen atom, a halogen atom, hydroxyl group and an organic group. When $R^5$ is a halogen atom, hydroxyl group or an organic group, $R^3$ is generally a leaving group (a group that can leave as $R^3H$). Such leaving groups include halogen atoms, hydroxyl group, substituted oxy groups such as alkoxy groups having about one to about ten carbon atoms, aryloxy groups, aralkyloxy groups, cycloalkyloxy groups, and acyloxy groups having about one to about ten carbon atoms.

$R^4$ is preferably an electron-withdrawing group. Examples of electron-withdrawing groups include acyl groups, carbonyl-protected acyl groups, substituted oxycarbonyl groups, carboxyl group, substituted or unsubstituted carbamoyl groups, cyano group, substituted or unsubstituted iminoalkyl groups, sulfur acid ester groups, aromatic hydrocarbon groups, aromatic heterocyclic groups, 1-alkenyl groups such as vinyl group and 1-propenyl group, 1-alkynyl groups such as ethynyl group, and haloalkyl groups.

Representative examples of unsaturated compounds represented by Formula (2) include alkenes such as ethylene, propylene, 1-butene, 2-butene, isobutene, 1-pentene, 2-pentene, 1-hexene, 2-hexene, 3-hexene, 1-heptene, 1-octene, 2-octene, 3-octene, 4-octene, 1-nonene, 1-decene, and 1-dodecene; alkadienes such as butadiene, 1,5-hexadiene, 1,6-heptadiene, and 1,7-octadiene, of which 1,3-alkadienes are preferred; styrenes such as styrene, vinyltoluene, and alpha-methylstyrene; heterocyclic compounds having vinyl group, such as 3-vinylpyridine, 3-vinylfuran, and 3-vinylthiophene; vinyl ethers such as methyl vinyl ether, ethyl vinyl ether, isopropyl vinyl ether, butyl vinyl ether, phenyl vinyl ether, benzyl vinyl ether, and pyridyl vinyl ether; vinyl esters such as vinyl acetate, isopropenyl acetate, vinyl propionate, isopropenyl propionate, vinyl butyrate, isopropenyl butyrate, vinyl isobutyrate, vinyl benzoate, and vinyl nicotinate; unsaturated carboxylic acids such as acrylic acid, maleic acid, and fumaric acid, or acid anhydrides thereof; acrylic esters such as methyl acrylate, ethyl acrylate, propyl acrylate, isopropyl acrylate, butyl acrylate, isobutyl acrylate, t-butyl acrylate, hexyl acrylate, octyl acrylate, 2-ethylhexyl acrylate, phenyl acrylate, benzyl acrylate, and cyclohexyl acrylate; crotonic esters such as methyl crotonate and ethyl crotonate; 3-phenylacrylic esters such as methyl 3-phenylacrylate and ethyl 3-phenylacrylate; 3-alkoxyacrylic esters such as methyl 3-methoxyacrylate, ethyl 3-methoxyacrylate, methyl 3-ethoxyacrylate, and ethyl 3-ethoxyacrylate; maleic esters such as dimethyl maleate, diethyl maleate, and diisopropyl maleate; fumaric esters such as dimethyl fumarate, diethyl fumarate, and diisopropyl fumarate; alpha,beta-unsaturated nitrites such as acrylonitrile, 3-methoxyacrylonitrile, and 3-ethoxyacrylonitrile; alpha, beta-unsaturated aldehydes such as acrolein, methacrolein, 3-methoxyacrolein, and 3-ethoxyacrolein; unsaturated alcohols such as allyl alcohol and geraniol; alpha,beta-unsaturated ketones such as methyl vinyl ketone, divinyl ketone, 4-methoxy-3-buten-2-one, 4-ethoxy-3-buten-2-one, 5-methoxy-4-penten-3-one, and 5-ethoxy-4-penten-3-one; and cyclic olefins including cycloalkenes and bridged hydrocarbons having a carbon-carbon double bond, such as cyclopentene, cyclohexene, cyclooctene, cyclodecene, cyclododecene, norbornene, dicyclopentadiene, and cyclooctadiene.

Among them, preferred are 1,3-alkadienes; styrenes; heterocyclic compounds having vinyl group; alpha,beta-unsaturated carboxylic acids or derivatives thereof, such as (meth) acrylic acids, maleic acid, fumaric acid, acrylic esters, crotonic esters, 3-phenylacrylic esters, 3-alkoxyacrylic esters, maleic esters, and fumaric esters; alpha,beta-unsaturated nitriles; alpha,beta-unsaturated aldehydes; and alpha, beta-unsaturated ketones.

Precursors of unsaturated compounds represented by Formula (2) include any compounds that can be converted into unsaturated compounds represented by Formula (2) under reaction conditions. Examples of such precursors include 3,3-dialkoxypropionic esters such as methyl 3,3-dimethoxypropionate, ethyl 3,3-dimethoxypropionate, methyl 3,3-diethoxypropionate, and ethyl 3,3-diethoxypropionate; 3,3-dialkoxypropionitriles such as 3,3-dimethoxypropionitrile and 3,3-diethoxypropionitrile; 3,3-dialkoxypropionaldehydes such as 3,3-dimethoxypropionaldehyde and 3,3-diethoxypropionaldehyde; beta-ketoacetals such as 4,4-dimethoxybutan-2-one, 4,4-diethoxybutan-2-one, 5,5-dimethoxypentan-3-one, and 5,5-diethoxypentan-3-one. The 3,3-dialkoxypropionic esters, 3,3-dialkoxypropionitriles, 3,3-dialkoxypropionaldehydes, and beta-ketoacetals are converted into 3-alkoxyacrylic esters, 3-alkoxyacrylonitriles, 3-alkoxyacroleins, and vinylalkyl ether compounds having vinyl group combined with an acyl group at the beta-position, respectively, in the system. The converted compounds then undergo a reaction with a compound represented by Formula (1) or an equivalent thereof.

Precursors of unsaturated compounds represented by Formula (2) further include 1,3-dicarbonyl compounds including beta-diketones such as 2,4-pentanedione (i.e., acetylacetone), 2,4-hexanedione, and 3,5-heptanedione; beta-ketoesters such as methyl acetoacetate and ethyl acetoacetate. These compounds are isomerized in the system into enol compounds corresponding to unsaturated compounds represented by Formula (2). The enol compounds then undergo a reaction with compound represented by Formula (1) or an equivalent thereof. For example, 2,4-pentanedione (i.e., acetylacetone) is enolized in the system into 2-hydroxy-2-penten-4-one and then undergoes a reaction with a compound represented by Formula (1) or an equivalent thereof.

Catalysts

A process according to an embodiment of the present invention does not always use a catalyst. A catalyst, however, may be used for promoting a reaction. Such catalysts include catalysts for use in oxidation reactions, such as catalytic platinum-group metal compounds. Among them, catalytic palladium compounds (A) are often used.

Catalytic palladium compounds (A) include, for example, zerovalent palladium compounds and divalent palladium compounds. The zerovalent palladium compounds include, for example, metal palladium (elementary palladium) and zerovalent palladium complexes. Examples of divalent palladium compounds include organic acid salts of divalent palladium, such as palladium(II) acetate and palladium(II) cyanide; organic complexes of divalent palladium, such as dichlorobis(benzonitrile)palladium(II); halides of divalent palladium, such as palladium(II) fluoride, palladium(II) chloride, palladium(II) bromide, and palladium(II) iodide; oxoacids of divalent palladium, such as palladium(II) nitrate and palladium(II) sulfate; palladium(II) oxide, palladium(II) sulfide, palladium(II) selenide, palladium(II) hydroxide, tetraamminepalladium(II) chloride, and other inorganic complexes of divalent palladium.

Of these palladium compounds, preferred are divalent palladium compounds including organic acid salts or organic complexes of divalent palladium, such as palladium(II) acetate and palladium(II) acetylacetonato [bis(acetylacetonato)palladium(II)]; halides of divalent palladium, such as palladium(II) chloride; and oxoacid salts of divalent palladium, such as palladium(II) sulfate.

Palladium compounds can be used as being supported by carriers such as activated carbon, silica, alumina, and zeolite. Palladium compounds for use herein further include natural minerals, such as hydrotalcite and hydroxyapatite, containing palladium as constitutional element. Each of these palladium compounds can be used alone or in combination.

The amount of palladium compounds is, for example, about 0.00001 to about 0.6 mole, preferably about 0.001 to about 0.5 mole, and more preferably about 0.05 to about 0.3 mole, per 1 mole of the compound used in a smaller amount between the two raw materials, i.e., the carbonyl compound represented by Formula (1) or an equivalent thereof and the unsaturated compound represented by Formula (2) or a precursor thereof.

Promoters

A promoter (co-catalyst) can be used in combination with a catalyst according to an embodiment of the present invention. When a catalytic palladium compound (A), for example, is used as the catalyst, a promoter (B) may be used in addition to the catalytic palladium compound (A), which promoter (B) includes a heteropolyacid or a salt thereof (B1); or a mixture of oxoacids and/or salts thereof (B2) containing, as a whole, an element selected from phosphorus and silicon and at least one element selected from vanadium, molybdenum, and tungsten. The use of a promoter (B) may contribute to increase in reaction rate and yield of a target compound.

In the heteropolyacid or a salt thereof (B1), the "heteropolyacid" is a condensate of oxoacids containing two or more different central ions and is also called as a heteronuclear condensed acid. Such heteropolyacids each contain, for example, an oxoacid ion of P, As, Sn, Si, Ti, or Zr, such as phosphoric acid or silicic acid, and another oxoacid ion of V, Mo, or W, such as vanadic acid, molybdic acid, or tungstic acid. Various heteropolyacids may occur as a result of combinations of these oxoacid ion.

Heteroatoms of oxoacids constituting the heteropolyacids are not specifically limited and include, for example, Cu, Be, B, Al, C, Si, Ge, Sn, Ti, Zr, Ce, Th, N, P, As, Sb, V, Nb, Ta, Cr, Mo, W, U, Se, Te, Mn, I, Fe, Co, Ni, Rh, Os, Ir, and Pt. Preferred heteropolyacids each contain at least one element selected from P, Si, V, Mo, and W and more preferably contain one of P and Si in combination with at least one selected from V, Mo and W. Heteropolyacids further more preferably contain one of P and Si in combination with at least one of V and Mo.

Heteropoly-anions constituting the heteropolyacids and salts thereof may have various compositions. Heteropoly-anions preferably have a composition represented by: $XM_{12}O_{40}$, wherein X is an element such as Si or P; and M is another element such as Mo, W, or V. Examples of heteropoly-anions having the composition are anions of phosphomolybdic acids, phosphotungstic acids, silicomolybdic acids, silicotungstic acids, and phosphovanadomolybdic acids.

The heteropolyacids may each be a free heteropolyacid, or a salt of heteropolyacid, except with another cation replacing at least part of hydrogen atoms corresponding to the cation of the heteropolyacid. Such cations capable of replacing the hydrogen atoms include, but are not limited to, cations of: ammonium such as $NH_4$; alkali metals such as Cs, Rb, K, Na, and Li; and alkaline earth metals such as Ba, Sr, Ca, and Mg.

Among these heteropolyacids and salts thereof, preferred are phosphovanadomolybdic acids and phosphomolybdic acids represented by the following formula:

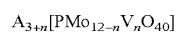

$A_{3+n}[PMo_{12-n}V_nO_{40}]$ wherein A is a heteropolyacid cation; and "n" represents an integer from 0 to 10 and is preferably an integer from 1 to 10, and salts of them.

Examples of the cation represented by "A" include hydrogen atom and the aforementioned cations. Among these heteropolyacids and salts thereof, typically preferred are fully protic phosphovanadomolybdic acids and phosphomolybdic acids (protic phosphovanadomolybdic acids and phosphomolybdic acids of perfect proton type). In this case, the number "n" is generally from 0 to 4 and preferably from 1 to 4. Examples of such fully protic phosphovanadomolybdic acids are $H_4PMo_{11}VO_{40}$, $H_5PMo_{10}V_2O_{40}$, $H_6PMo_9V_3O_{40}$, and $H_7PMo_8V_4O_{40}$.

The heteropolyacids and salts thereof may be anhydrous or may contain crystal water. They can be used as being supported by carriers such as activated carbon. In this case, a heteropolyacid or a salt thereof and a palladium compound may be dispersed and supported on one carrier. Each of these heteropolyacids and salts thereof can be used alone or in combination.

The mixtures of oxoacids and/or salts thereof (B2) are not specifically limited as long as they are mixtures each containing, as a whole, one of P and Si, and at least one element selected from V, Mo, and W. The term "oxoacid" as used herein also includes heteropolyacids. In contrast, the term "oxoacid in the narrow sense" does not include such heteropolyacids.

Such heteropolyacids containing P, Si, V, Mo, and/or W include, but are not limited to, phosphomolybdic acid, phosphotungstic acid, phosphovanadic acid, phosphovanadomolybdic acid, silicomolybdic acid, silicotungstic acid, and silicovanadic acid. The oxoacids in the narrow sense containing one of P, Si, V, Mo, and W include, but are not limited to, phosphoric acid, silicic acid, vanadic acid, molybdic acid, and tungstic acid. Salts of these heteropolyacids and oxoacids in the narrow sense include, for example, ammonium salts, alkali metal salts, and alkaline earth metal salts.

Mixtures of oxoacids and/or salts thereof (B2) can be categorized typically as (i) a mixture of two or more different heteropolyacids and/or salts thereof, such as a mixture of phosphomolybdic acid or a salt thereof with phosphovanadic acid or a salt thereof; (ii) a mixture of a heteropolyacid and/or a salt thereof with an oxoacid in the narrow sense or a salt thereof, such as a mixture of phosphomolybdic acid or a salt thereof with vanadic acid or a salt thereof, and a mixture of a phosphovanadic acid or a salt thereof with molybdic acid or a salt thereof; and (iii) a mixture of two or more different oxoacids in the narrow sense and/or salts thereof, such as a mixture of phosphoric acid or a salt thereof, molybdic acid or a salt thereof, and vanadic acid or a salt thereof. These oxoacids and salts thereof may be anhydrous or may contain crystal water.

In the heteropolyacids or salts thereof (B1), proportions of respective elements can be adjusted within the above-specified ranges by mixing two or more heteropolyacids and/or salts thereof having different compositions. Such a promoter (co-catalyst) having proportions of respective elements within the above-specified ranges can be prepared, for example, by mixing two or more of the phosphovanadomolybdic acids and/or salts thereof represented by the formula: $A_{3+n}[PMo_{12-n}V_nO_{40}]$, wherein "n" is from 1 to 10, or by mixing a phosphovanadomolybdic acid or a salt thereof represented by the formula: $A_{3+n}[PMo_{12-n}V_nO_{40}]$, wherein "n" is from 1 to 10, with a phosphomolybdic acid or a salt thereof represented by the formula: $A_3PMo_{12}O_{40}$.

The amount of promoters (B) is not specifically limited and is, for example, about 0.00001 to about 0.5 mole, preferably about 0.0001 to about 0.1 mole, and more preferably about 0.001 to about 0.05 mole, per 1 mole of the compound used in a smaller amount between the two raw materials, i.e., the carbonyl compound represented by Formula (1) or an equivalent thereof and the unsaturated compound represented by Formula (2) or a precursor thereof.

When the catalytic palladium compound (A) is used, a Lewis acid (C) can be used in addition to the catalytic palladium compound (A) or in addition to the catalytic palladium compound (A) and the promoter (B). By using a Lewis acid (C), the reaction rate and the yield of a target compound may increase.

Lewis acids (C) are not specifically limited and include, for example, compounds containing any of Groups 3, 4, 12, 13, 14, and 15 elements of the Periodic Table of Elements. Each of Lewis acids can be used alone or in combination. Of the Periodic Table of Elements, the Group 3 elements include scandium; yttrium; lanthanoids such as lanthanum, cerium, praseodymium, neodymium, samarium, gadolinium, and ytterbium; and actinoids such as actinium and thorium. The Group 4 elements include titanium, zirconium, and hafnium. The Group 12 elements include zinc and cadmium. The Group 13 elements include boron, aluminum, gallium, indium, and thallium. The Group 14 elements include, for example, silicon, germanium, tin, and lead. Group 15 elements include, for example, antimony and bismuth. Compounds containing these elements include triflates (trifluoromethanesulfonates) and halides, such as fluorides, chlorides, bromides, and iodides, of these elements.

Representative examples of Lewis acids include halides or triflates of Group 3 elements, such as cerium chloride ($CeCl_3$), gadolinium chloride ($GdCl_3$), ytterbium triflate [$Yb(OTf)_3$], samarium triflate [$Sm(OTf)_3$], and gadolinium triflate [$Gd(OTf)_3$]; halides or triflates of Group 4 elements, such as zirconium chloride ($ZrCl_2$); halides or triflates of Group 12 elements such as zinc chloride ($ZnCl_2$); halides or triflates of Group 13 elements, such as indium chloride ($InCl_3$) and indium bromide ($InBr_3$); halides or triflates of Group 14 elements, such as tin chloride ($SnCl_2$); halides or triflates of Group 15 elements, such as bismuth chloride. Of these, preferred are halides or triflates of Group 3 elements.

The amount of Lewis acids is, for example, about 0.00001 to about 0.6 mole, preferably about 0.001 to about 0.5 mole, and more preferably about 0.05 to about 0.3 mole, per 1 mole of the compound used in a smaller amount between the two raw materials, i.e., the carbonyl compound represented by Formula (1) or an equivalent thereof and the unsaturated compound represented by Formula (2) or a precursor thereof.

In a process according to an embodiment of the present invention, a compound capable of coordinating with palladium (coordinating compound) may be added to the reaction system, for increasing the reaction rate and/or improving the selectivity of the reaction.

Reaction

The reaction is carried out in the presence of, or in the absence of a solvent. The reaction is preferably conducted in the presence of a solvent. The solvent can be selected as appropriate according typically to the types of raw materials. Examples of such solvents include organic acids including carboxylic acids such as acetic acid, propionic acid, and trifluoroacetic acid; amides such as formamide, acetamide, dimethylformamide (DMF), and dimethylacetamide; nitro compounds such as nitromethane and nitroethane; esters such as ethyl acetate and butyl acetate; ketones such as acetone and methyl ethyl ketone; chain or cyclic ethers such as diethyl ether, diisopropyl ether, dimethoxyethane, tetrahydrofuran, and dioxane; alcohols such as methanol, ethanol, propanol, butanol, and t-butyl alcohol; aliphatic hydrocarbons such as hexane and octane; alicyclic hydrocarbons such as cyclopentane, cyclohexane, and methylcyclohexane; halogenated hydrocarbons such as chloroform, dichloromethane, dichloroethane, and carbon tetrachloride; water; and mixtures of these solvents. Of these, preferred are protic solvents containing oxygen atom, such as solvents having a —OH structure. More specific examples thereof include alcohols such as methanol and ethanol; organic acids including carboxylic acids such as acetic acid and propionic acid; and mixtures of these solvents. Oxygen atom in these solvents can be introduced into a target compound.

The ratio of a carbonyl compound represented by Formula (1) or an equivalent thereof to an unsaturated compound represented by Formula (2) or a precursor thereof can be set as appropriate according typically to the types and combination of the two compounds. The ratio in terms of molar ratio is generally about 0.8 to about 50, preferably about 1.5 to about 30, and more preferably about 2 to about 20, in view typically of reactivity.

A polymerization inhibitor such as hydroquinone may be added to the reaction system, so as to prevent polymerization of unsaturated compounds.

Oxygen

A reaction in a process according to an embodiment of the present invention can be carried out in the presence of or in the absence of oxygen, but is preferably carried out in the presence of oxygen. The oxygen can act as a reoxidizing agent for catalysts such as palladium compounds. The oxygen is preferably molecular oxygen. The molecular oxygen is not specifically limited and can be pure oxygen, air, or oxygen diluted with an inert gas such as nitrogen, helium, or argon.

The amount of oxygen in terms of $O_2$ is generally about 0.5 mole or more, for example, about 1 mole or more, preferably about 1 to about 100 moles, and more preferably about 1 to about 50 moles, per 1 mole of the compound used in a smaller amount between the two raw materials, i.e., the carbonyl compound represented by Formula (1) or an equivalent thereof and the unsaturated compound represented by Formula (2) or a precursor thereof. Oxygen can be used in large excess.

A reaction in a process according to an embodiment of the present invention can smoothly proceed even under relatively mild conditions. A reaction temperature can be set as appropriate according typically to the types of raw materials and is generally about 0° C. to about 200° C., preferably about 40° C. to about 150° C., and more preferably about 60° C. to about 120° C. The reaction may be carried out under normal pressure or under a pressure (under a load). The reaction may be carried out preferably in the presence of or under flow of oxygen. It can be carried out according to a conventional system such as a batch system, a semi-batch system, or a continuous system. The order of addition of components such as reaction components and catalysts is not specifically limited. The addition may be carried out, for example, (i) by adding a mixture containing a carbonyl compound represented by Formula (1) or an equivalent thereof and an unsaturated compound represented by Formula (2) or a precursor thereof dropwise to a mixture containing a catalyst and where necessary further containing a promoter and/or a Lewis acid, or (ii) by adding a solution containing a carbonyl compound represented by Formula (1) or an equivalent thereof dropwise to a mixture containing a catalyst and an unsaturated compound represented by Formula (2) or a precursor thereof and where necessary further containing a promoter and/or a Lewis acid.

According to such a process, a coupling reaction proceeds between a carbonyl compound represented by Formula (1) or an equivalent thereof and an unsaturated compound represented by Formula (2) to thereby yield a furan compound represented by Formula (3). In Formula (3), $R^{3'}$ represents $R^3$, $R^5$ or hydrogen atom; and $R^1$, $R^2$, $R^3$, $R^4$, and $R^5$ are as defined above. When $R^5$ is hydrogen atom, $R^{3'}$ is generally $R^3$, but $R^{3'}$ may be hydrogen atom when $R^3$ is a leaving group such as a halogen atom or a substituted oxy group, because a de-$R^3H$ reaction may occur. In contrast, when $R^5$ is another group than hydrogen atom, such as a halogen atom or an organic group, and $R^3$ is a leaving group such as a halogen atom or a substituted oxy group, a de-$R^3H$ reaction occurs and $R^{3'}$ becomes $R^5$. When $R^4$ is a hydrolyzable group, such as a substituted oxycarbonyl group, and water is present in the reaction system, a corresponding hydrolysate such as a carboxylic acid may be formed.

After the completion of reaction, reaction products can be separated and purified by a separation procedure such as filtration, concentration, distillation, extraction, crystallization, recrystallization, adsorption, or column chromatography, or any combination of these separation procedures.

Furan compounds prepared by a process according to an embodiment of the present invention can be used, for example, as raw materials for polymers, intermediates for the synthetic preparation of highly functional materials and fine chemicals such as dyestuffs and pharmaceutical preparations, and intermediate materials for other organic chemicals.

EXAMPLES

The present invention will be illustrated in further detail with reference to several examples below. It should be noted, however, that these are illustrated only by way of example and are never intended to limit the scope of the present invention.

Example 1

In a reactor were placed palladium(II) acetate [Pd(OAc)$_2$] (0.2 mmol), $H_4PMo_{11}V_1O_{40}$ (15 μmol), cerium chloride heptahydrate (CeCl$_3$·7H$_2$O) (0.2 mmol), methanol (30 mmol), and acetic acid (4.5 ml); the mixture was raised in temperature to 70° C.; a mixture of methyl acrylate (1 mmol), propionaldehyde (6 mmol), and acetic acid (0.5 ml) was added at a rate of 5 μl/min in an oxygen atmosphere at 1 atm (0.1 MPa) using a syringe pump, and a reaction was conducted for eight hours. After the reaction, the reaction mixture was analyzed by gas chromatography to find that methyl 5-methylfuran-3-carboxylate was produced in a yield of 90%.

Example 2

A reaction was carried out by the procedure of Example 1, except for using bis(acetylacetonato)palladium(II) (palladium(II) acetylacetonate) [Pd (acac)$_2$] instead of palladium (II) acetate. After the reaction, the reaction mixture was analyzed by gas chromatography to find that methyl 5-methylfuran-3-carboxylate was produced in a yield of 90%.

Example 3

A reaction was carried out by the procedure of Example 1, except for using ethyl acrylate instead of methyl acrylate. After the reaction, the reaction mixture was analyzed by gas chromatography to find that ethyl 5-methylfuran-3-carboxylate was produced in a yield of 78%.

Example 4

A reaction was carried out by the procedure of Example 1, except for using butyl acrylate instead of methyl acrylate. After the reaction, the reaction mixture was analyzed by gas chromatography to find that butyl 5-methylfuran-3-carboxylate was produced in a yield of 65%.

Example 5

A reaction was carried out by the procedure of Example 1, except for using ethyl crotonate instead of methyl acrylate.

After the reaction, the reaction mixture was analyzed by gas chromatography to find that ethyl 2,5-dimethylfuran-3-carboxylate was produced in a yield of 12%.

Example 6

A reaction was carried out by the procedure of Example 2, except for using acrylonitrile instead of methyl acrylate. After the reaction, the reaction mixture was analyzed by gas chromatography to find that 5-methylfuran-3-carbonitrile was produced in a yield of 7%.

Example 7

A reaction was carried out by the procedure of Example 1, except for using acetaldehyde instead of propionaldehyde. After the reaction, the reaction mixture was analyzed by gas chromatography to find that 3-carbomethoxyfuran was produced in a yield of 5%.

Example 8

A reaction was carried out by the procedure of Example 1, except for using paraldehyde instead of propionaldehyde. After the reaction, the reaction mixture was analyzed by gas chromatography to find that 3-carbomethoxyfuran was produced in a yield of 3%.

Example 9

A reaction was carried out by the procedure of Example 8, except for placing paraldehyde initially in the reactor, raising the temperature to 70° C., and feeding a solution of methyl acrylate in acetic acid to the reactor using a syringe pump. After the reaction, the reaction mixture was analyzed by gas chromatography to find that 3-carbomethoxyfuran was produced in a yield of 25%.

Example 10

A reaction was carried out by the procedure of Example 9, except for placing paraldehyde initially in the reactor, stirring the mixture at 80° C., feeding a solution of methyl acrylate in acetic acid to the reactor using a syringe pump, and carrying out a reaction at 80° C. for eight hours. After the reaction, the reaction mixture was analyzed by gas chromatography to find that 3-carbomethoxyfuran was produced in a yield of 45%.

Example 11

A reaction was carried out by the procedure of Example 1, except for using butyraldehyde instead of propionaldehyde. After the reaction, the reaction mixture was analyzed by gas chromatography to find that methyl 5-ethylfuran-3-carboxylate was produced in a yield of 56%.

Example 12

A reaction was carried out by the procedure of Example 1, except for using isoamylaldehyde instead of propionaldehyde. After the reaction, the reaction mixture was analyzed by gas chromatography to find that methyl 5-isopropylfuran-3-carboxylate was produced in a yield of 34%.

Example 13

A reaction was carried out by the procedure of Example 1, except for using methyl ethyl ketone instead of propionaldehyde. After the reaction, the reaction mixture was analyzed by gas chromatography to find that methyl 4,5-dimethylfuran-3-carboxylate was produced in a yield of 3%.

Example 14

A reaction was carried out by the procedure of Example 1, except for using methyl vinyl ketone instead of methyl acrylate. After the reaction, the reaction mixture was analyzed by gas chromatography to find that 3-acetyl-5-methylfuran was produced in a yield of 35%.

Example 15

A reaction was carried out by the procedure of Example 1, except for using ethyl 3,3-diethoxypropionate instead of methyl acrylate. After the reaction, the reaction mixture was analyzed by gas chromatography to find that ethyl 5-methylfuran-3-carboxylate was produced in a yield of 56%.

Example 16

In a reactor were placed bis(acetylacetonato)palladium(II) [Pd (acac)$_2$] (0.3 mmol), $H_4PMo_{11}V_1O_{40}$ (23 µmol), cerium chloride heptahydrate ($CeCl_3 \cdot 7H_2O$) (0.3 mmol), methanol (1 ml), and acetic acid (4.5 ml); the mixture was raised in temperature to 80° C.; a solution of 2,4-pentanedione (1 mmol) and propionaldehyde (10 mmol) in acetic acid (0.5 ml) was fed to the mixture in an oxygen atmosphere at 1 atm (0.1 MPa) over three hours using a syringe pump; and a reaction was carried out for a total of eight hours. After the reaction, the reaction mixture was analyzed by gas chromatography to find that 2,5-dimethyl-3-acetylfuran was produced in a yield of 94%.

Example 17

In a reactor were placed palladium(II) acetate [Pd(OAc)$_2$] (0.3 mmol), $H_4PMo_{11}V_1O_{40}$ (23 µmol), cerium chloride heptahydrate ($CeCl_3 \cdot 7H_2O$) (0.3 mmol), methanol (1 ml), and acetic acid (4.5 ml); the mixture was raised in temperature to 80° C.; a solution of methyl acrylate (1 mmol) and n-butyraldehyde (7 mmol) in acetic acid (0.5 ml) was added to the mixture in an-oxygen atmosphere at 1 atm (0.1 MPa) over three hours using a syringe pump; and a reaction was carried out for a total of eight hours. After the reaction, the reaction mixture was analyzed by gas chromatography to find that 2-ethyl-4-carbomethoxyfuran (i.e., methyl 5-ethylfuran-3-carboxylate) was produced in a yield of 83%.

Example 18

In a reactor were placed palladium(II) acetate [Pd(OAc)$_2$] (0.3 mmol), $H_4PMo_{11}V_1O_{40}$ (23 µmol), cerium chloride heptahydrate ($CeCl_3 \cdot 7H_2O$) (0.3 mmol), methanol (1 ml), andacetic acid (4.5 ml); the mixture was raised in temperature to 80° C.; a solution of methyl acrylate (1 mmol) and isovaleraldehyde (7 mmol) in acetic acid (0.5 ml) was added to the mixture in an oxygen atmosphere at 1 atm (0.1 MPa) over three hours using a syringe pump; and a reaction was carried out for a total of eight hours. After the reaction, the reaction mixture was analyzed by gas chromatography to find that 2-isopropyl-4-carbomethoxyfuran (i.e., methyl 5-isopropylfuran-3-carboxylate) was produced in a yield of 24%.

It should be understood by those skilled in the art that various modifications, combinations, subcombinations, and alterations may occur depending on design requirements and other factors insofar as they are within the scope of the appended claims or the equivalents thereof.

What is claimed is:

1. A process for the preparation of furan compounds, the process comprising the step of:

carrying out a reaction of a carbonyl compound represented by following Formula (1):

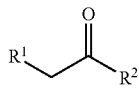

(1)

wherein $R^1$ represents hydrogen atom or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other; and $R^2$ represents hydrogen atom or a group having a carbon atom at a bonding site with the carbonyl group in Formula (1) and having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other, wherein $R^1$ and $R^2$ may be combined to form a ring with adjacent two carbon atoms, or a multimer of carbonyl compounds, or a carbonyl-protected derivative that yields the same reaction product as the carbonyl compound represented by Formula (1), with an unsaturated compound represented by following Formula (2) or a compound converted into the unsaturated compound represented by Formula (2) during carrying out the reaction and selected from a group consisting of 3,3-dialkoxypropionic ester, 3,3-dialkoxypropionitrile, 3,3-dialkoxypropionaldehyde, beta-ketoacetal; and beta-diketone:

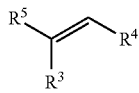

(2)

wherein $R^5$ wherein represents hydrogen atom, a halogen atom, hydroxyl group, or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other, wherein in the unsaturated compound represented by formula (2), when $R^5$ is hydrogen atom, $R^3$ is any one of hydrogen atom, a halogen atom, hydroxyl group or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other, and when $R^5$ is a halogen atom, hydroxyl group or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other, $R^3$ is a leaving group, and wherein leaving group is defined as a group that leaves as $R^3H$ during the reaction wherein $R^4$ is an electron-withdrawing group, to yield a furan compound represented by following Formula (3):

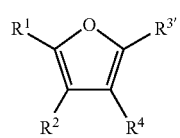

(3)

wherein $R^{3'}$ represents $R^3$, $R^5$ or hydrogen atom; and $R^1$, $R^2$, $R^3$, $R^4$, are $R^5$ are as defined above.

2. The process according to claim 1, wherein the reaction is carried out in the presence of a catalytic palladium compound (A).

3. The process according to claim 2, wherein the reaction is carried out in the presence of a promoter (B) in addition to the catalytic palladium compound (A), and wherein the promoter (B) comprises:

a heteropolyacid or a salt thereof (B1); or a mixture of oxoacids and/or salts thereof (B2) containing, as a whole, an element selected from phosphorus and silicon and at least one element selected from vanadium, molybdenum, and tungsten.

4. The process according to claim 3, wherein the heteropolyacid or a salt thereof (B1) comprises an element selected from phosphorus and silicon and at least one element selected from vanadium, molybdenum, and tungsten as constitutional elements.

5. The process according to one of claims 3 and 4, wherein the heteropolyacid or a salt thereof (B1) comprises a phosphovanadomolybdic acid or phosphomolybdic acid represented by following Formula:

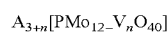

wherein "A" represents at least one selected from the group consisting of hydrogen atom, $NH_4$, alkali metals, and alkaline earth metals; and "n" represents an integer of 0 to 10, or a salt of them.

6. The process according to claim 2, wherein the reaction is carried out in the presence of a Lewis acid (C), in addition to the catalytic palladium compound (A).

7. The process according to claim 1, wherein $R^3$ in formula (2) is a leaving group selected from the group consisting of halogen atom, hydroxyl group and substituted oxy group.

8. A process for the preparation of furan compounds, the process comprising the step of:
carrying out a reaction of a carbonyl compound represented by following Formula (1) in the presence of a catalytic palladium compound (A):

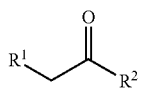

(1)

wherein $R^1$ represents an hydrogen atom, substituted or unsubstituted hydrocarbon groups including aliphatic hydrocarbon groups having about one to about twenty carbon atoms, aromatic hydrocarbon groups having about six to about twenty carbon atoms, alicyclic hydrocarbon groups having about three to about twenty carbon atoms, bridged hydrocarbon groups, haloalkyl groups having about one to about six carbon atoms, heterocyclic groups; alkoxy groups having about one to about ten carbon atoms, aryloxy groups, aralkyloxy groups, cycloalkyloxy groups, and acyloxy groups having about one to about ten carbon atoms, acyl groups, carbonyl-protected acyl groups, substituted oxycarbonyl groups including alkoxy-carbonyl groups having about one to about six carbon atoms in the alkoxy moiety, aryloxycarbonyl groups, aralkyloxycarbonyl groups, and cycloalkyloxycarbonyl groups, substituted or unsubstituted carbamoyl groups, cyano groups, or sulfur acid ester groups ; and
$R^2$ represents an hydrogen atom, substituted or unsubstituted hydrocarbon groups having about one to about twenty carbon atoms, aromatic hydrocarbon groups having about six to about twenty carbon atoms, alicyclic hydrocarbon groups having about three to about twenty carbon atoms, bridged hydrocarbon groups and haloalkyl groups having about one to about six carbon atoms, or heterocyclic groups, wherein $R^1$ and $R^2$ may be combined to form a ring with adjacent two carbon atoms, with an unsaturated compound represented by following Formula (2):

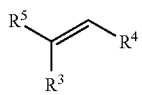

(2)

wherein $R^5$ represents hydrogen atom, a halogen atom, hydroxyl group, or an organic group,
wherein when $R^5$ is hydrogen atom, $R^3$ is any of hydrogen atom, a halogen atom, hydroxyl group and an organic group,
and when $R^5$ is a halogen atom, hydroxyl group or an organic group, $R^3$ is a leaving group wherein leaving group is defined as a group that leaves as $R^3H$ during the reaction, and
wherein $R^4$ is an electron-withdrawing group, to yield a furan compound represented by following Formula (3):

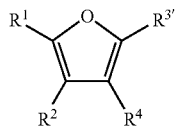

(3)

wherein $R^{3'}$ represents $R^3$, $R^5$ or hydrogen atom; and $R^1$, $R^2$, $R^3$, $R^4$, are $R^5$ are as defined above.

9. A process for the preparation of furan compounds, the process comprising the step of:
carrying out a reaction of a carbonyl compound represented by following Formula (1) in the presence of a catalytic palladium compound (A) and a promoter (B):

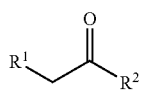

(1)

wherein each of $R^1$ and $R^2$ represents an hydrogen atom or a hydrocarbon group having one to about twenty carbon atoms, wherein $R^1$ and $R^2$ may be combined to form a ring with adjacent two carbon atoms, or a multimer of carbonyl compounds, or a carbonyl protected derivative that yields the same reaction product as the carbonyl compound represented by Formula (1) with an unsaturated compound represented by following Formula (2):

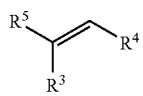

(2)

wherein $R^5$ represents a hydrogen atom, a halogen atom, hydroxyl group, or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other,
wherein when $R^5$ is hydrogen atom, $R^3$ is any of a hydrogen atom, a halogen atom, hydroxyl group or a group having one to twenty carbon atoms selected from a group consisting of hydrocarbon group, heterocyclic group, substituted oxy group, N-substituted amino groups, acyl groups and carbonyl-protected derivatives thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other,
and when $R^5$ is a halogen atom, hydroxyl group or a group having one to twenty carbon atoms selected from a group consisting of hydrocarbon group, heterocyclic group, substituted oxy group, N-substituted amino groups, acyl groups and carbonyl-protected derivative thereof, substituted oxycarbonyl groups, carboxyl group unprotected or protected by protecting groups, substituted or unsubstituted carbamoyl groups, cyano group, substituted or unsubstituted iminoalkyl group, sulfur acid ester group, and a group containing two or more of these groups combined with each other $R^3$ is a leaving group, wherein leaving group is defined as a group that leaves as $R^3H$ during the reaction, and
wherein $R^4$ is an electron-withdrawing group,
or a compound selected from a group consisting of 3,3-dialkoxypropionic ester, 3,3-dialkoxypropionitrile, 3,3-dialkoxypropionaldehyde, beta-ketoacetal and beta-diketone,
to yield a furan compound represented by following Formula (3):

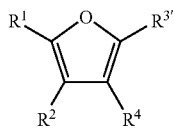

(3)

wherein $R^{3\prime}$ represents $R^3$, $R^5$ or hydrogen atom; and $R^1$, $R^2$, $R^3$, $R^4$, are $R^5$ are as defined above,
wherein the promoter (B) comprises a heteropolyacid or a salt thereof (B1) comprising an element selected from phosphorus and silicon and at least one element selected from vanadium, molybdenum and tungsten as constitutional elements; or
a mixture of oxoacids and/or salts thereof (B2) containing as a whole, an element selected from phosphorus and silicon and at least one element selected from vanadium, molybdenum, and tungsten.

* * * * *